United States Patent
Krstevich et al.

Patent Number: 5,329,937
Date of Patent: Jul. 19, 1994

[54] SPECULUM PROTECTOR WITH SMOKE TUBE

[75] Inventors: Stephen Krstevich, Northville; Fredrick Kamienny, Bloomfield Hills; Frederick Erlich, Farmington Hills; Steve Watkins, St. Clair Shores, all of Mich.

[73] Assignee: Nova Healthcare Industries, Inc., Madison Heights, Mich.

[21] Appl. No.: 943,319

[22] Filed: Sep. 10, 1992

[51] Int. Cl.$^5$ .............................. A61B 1/32
[52] U.S. Cl. ........................... 128/17; 128/3; 604/268
[58] Field of Search ............ 128/17, 3, 10–13, 128/18, 15, 16, 4; 604/21, 27, 48, 104, 106, 171, 268, 279

[56] References Cited

U.S. PATENT DOCUMENTS

| | | | |
|---|---|---|---|
| 2,483,233 | 9/1949 | Price et al. | 604/106 X |
| 2,672,859 | 3/1954 | Jones | 604/106 X |
| 3,769,968 | 11/1973 | Blount et al. | 128/17 |
| 4,492,220 | 1/1985 | Hayes | 128/17 |
| 4,562,832 | 1/1986 | Wilder et al. | 128/20 |
| 4,597,382 | 7/1986 | Perez, Jr. | 128/17 |
| 4,807,600 | 2/1989 | Hayes | 128/17 |
| 4,884,558 | 12/1989 | Gorski et al. | 128/11 |
| 4,884,559 | 12/1989 | Collins | 128/17 |
| 4,972,825 | 11/1990 | Vescovo, Jr. | 128/3 X |
| 4,979,499 | 12/1990 | Sun | 128/16 X |
| 5,007,409 | 4/1991 | Pope | 128/3 X |
| 5,025,778 | 6/1991 | Silverstein et al. | 128/4 |
| 5,063,908 | 11/1991 | Collins | 128/17 |
| 5,120,304 | 6/1992 | Sasaki | 604/27 X |
| 5,143,054 | 9/1992 | Adair | 128/18 |
| 5,179,938 | 1/1993 | Lonky | 128/18 |
| 5,217,001 | 6/1993 | Nakao et al. | 128/4 |

OTHER PUBLICATIONS

Euro–Med/Cooper Surgical Catalog, Winter/Spring 1992.

Primary Examiner—Richard J. Apley
Assistant Examiner—Donna L. Maraglio
Attorney, Agent, or Firm—Reising, Ethington, Barnard, Perry & Milton

[57] ABSTRACT

A speculum cover for a speculum blade has a smoke tube associated therewith. The speculum cover may be removable from the blade.

6 Claims, 1 Drawing Sheet

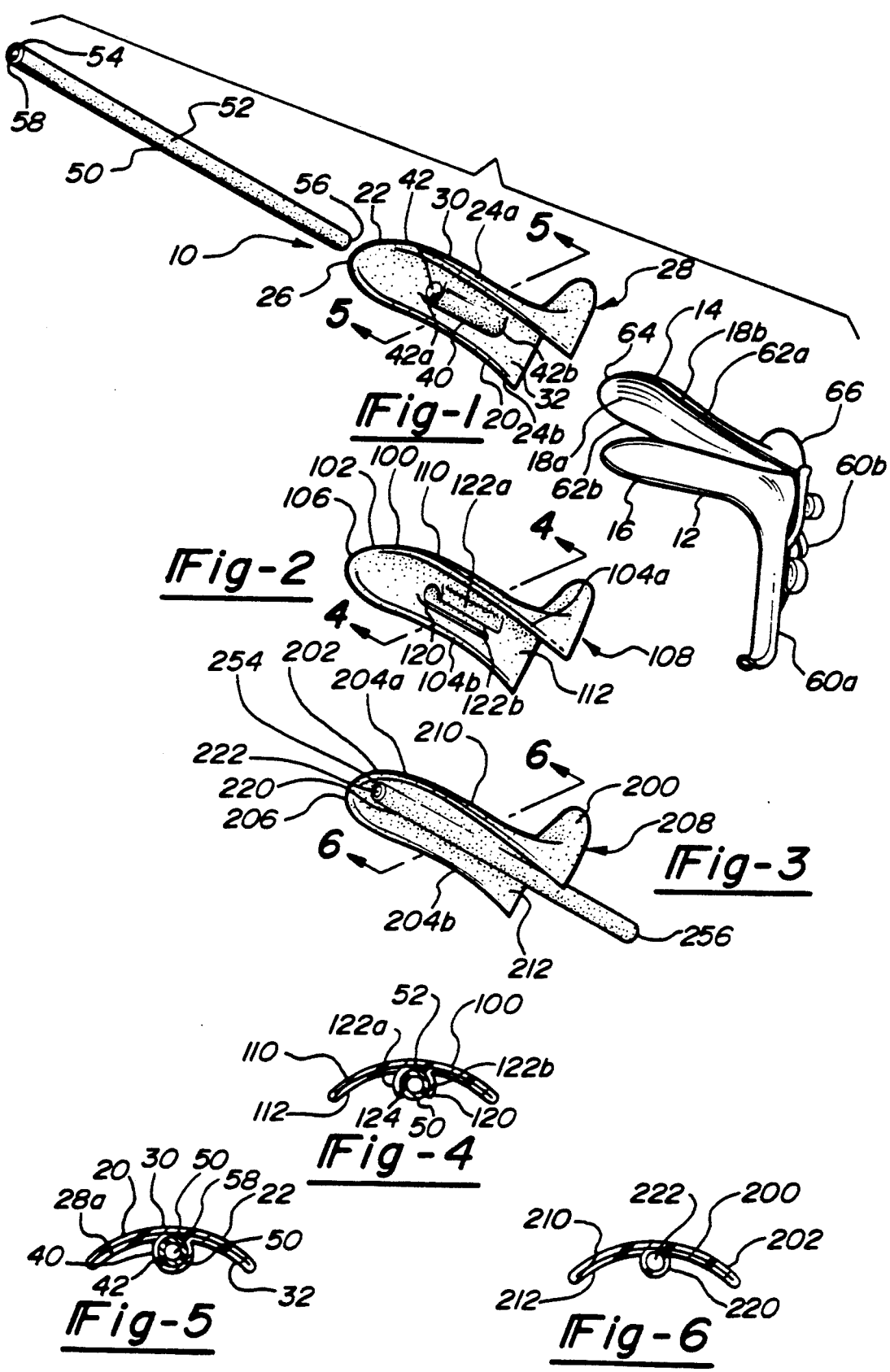

SPECULUM PROTECTOR WITH SMOKE TUBE

BACKGROUND OF THE INVENTION

1. Field Of Invention

This invention relates to surgical speculums, more particularly to vaginal speculums; even more particularly to such speculum devices for preventing cross contamination and removal of smoke during vaginal surgery.

2. Prior Art

A vaginal speculum is a medical instrument commonly used for examination and treatment of the vagina and related areas. A typical vaginal speculum is made of metal such as stainless steel. They are commonly comprised of a frame assembly having a pair of protruding blades which are inserted into the vagina. The blades are manually separated or opened providing a viewing or access channel for the medical practitioners. These instruments required extensive sterilization after being used.

Because of the difficulty of insuring absolute sterility, disposable covers were developed for use on the blades of the speculum. A typical example is found in U.S. Pat. No. 4,597,382 which discloses a pair of liquid absorbent sleeves that are placed on the blades of the speculum before use. The sleeves have the same shape as the blades and are disposed of after use. The use of the sleeve limits the exposure of the speculum's metal blades to contamination.

In U.S. Pat. Nos. 4,492,220, 4,807,600 as well as U.S. application Ser. No. 07/657,078 (pending), the disclosures of which are hereby incorporated by reference improved speculum blade cover or protector. The patents and application disclose a speculum protector which is a flexible plastic cover that is the same shape as the speculum blade. The cover is placed on the blade before use and removed from the blade and disposed of after use.

However, the above-described speculum and speculum blade covers disclosed in the aforesaid patents, which are hereby incorporated by reference, are of limited use with vaginal surgical procedures which produce a large amount of smoke such as laser surgery and electrical or high heat cauterizing of tissue. A method is needed to remove the smoke.

A common method of removing smoke from the surgical area is through a smoke tube, usually attached directly to a speculum and connected to a vacuum system. A typical smoke tube is made from a flexible plastic material and can be easily disposed after use. Examples of this type of speculum with smoke tubes are disclosed in Euro-Med/Cooper Surgical Catalog, Winter/Spring 1992 edition.

Another example of a smoke removing method is a metallic suction tube which is attached to the speculum's blade, usually by welding. This type of speculum is also disclosed in the Euro-Med/Cooper Surgical catalog.

The attachment of disposable smoke tubes directly to speculums or the attachment of permanent metal smoke tubes to speculums have similar problems and disadvantages:

(a) The attachment mounts for the disposable tubes and the permanently attached smoke tubes are usually made of the same material as the speculum. They become contaminated and will require the same sterilization as the speculum;

(b) The attachment mounts and attached smoke tubes are not flexible and can cause the patient discomfort and perhaps injury; and (c) The attached mounts and smoke tubes are attached at one location which is permanent thereby reducing flexibility during use.

SUMMARY OF INVENTION

The present invention provides for a smoke removal device that addresses the advantages of the speculums with permanently attached tube mounts or smoke tubes. The flexible disposable cover hereof having a smoke tube provides all the recognized advantages of a cover while at the same time improving the removal of smoke from the area of surgery.

Pursuant to the present invention, a vaginal protector or cover assembly including a smoke tube is provided for surgical use with a speculum of the type including a lower blade and an upper blade with opposing concavo-convex blade surfaces that can be separated or opened to provide a channel therebetween for viewing of or surgery upon the patient, the blade cover assembly comprising:

(a) a blade cover, the blade cover having an elastic hollow sleeve-like body with opposing side edges, a closed end and an outwardly open flared end adapted to be placed either permanently or disposably in covering protective relation over a speculum blade.

(b) a tube mount, the tube mount disposed on the lower surface of the blade cover, the tube mount having a cavity formed therethrough.

(c) a smoke tube, the tube being insertably disposed within the cavity of the tube mount.

The blade cover assembly hereof may be used with a second blade cover assembly which is fitted upon the opposite speculum blade, thus, providing two smoke tubes. The most common use of the blade cover assembly will be with a flexible blade cover fitted on the opposite blade with no smoke tube attached thereof.

In one embodiment of the invention, the smoke tube is inserted through the cavity in the tube mount and adjusted to a position desired by the medical practitioner. In this embodiment the tube urges against the wall of the cavity with sufficient pressure to prevent casual movement, but still provides for manual adjustment. After use, the tube and cover may be disposed of or the tube, alone, may be removed during use and disposed of, it necessary.

In a second embodiment of the invention, the smoke tube is inserted into a tube mount having flexible sides which grip the tube once it is in place. The sides of the mount urge against the tube with sufficient pressure to prevent the casual movement of the tube, but still provide for manual adjustment. After use, the tube and cover may be disposed of or the tube, alone, may be removed during use and disposed of if necessary.

In a third embodiment hereof, a smoke tube is integrally formed as one piece with at least one of the blade covers on the concave surface and a vacuum is connectable to one end of the tube.

For a more complete understanding of the blade cover assembly of the present invention, reference is made to the following description and accompanying drawings. Throughout the following description and drawings, identical reference numbers referred to the same component throughout the several views, in which:

BRIEF DESCRIPTION OF DRAWINGS

FIG. 1 is an exploded perspective view of a blade cover assembly n accordance herewith;

FIG. 2 is a perspective view of the second embodiment of the blade cover assembly hereof;

FIG. 3 is a perspective view of a third embodiment hereof;

FIG. 4 is a cross-sectional view along 4—4 of FIG. 2;

FIG. 5 is a cross-sectional view along 5—5 of FIG. 1; and

FIG. 6 is a cross-sectional view along 6—6 of FIG. 3.

DETAILED DESCRIPTION

Referring now to the drawings, and specifically FIGS. 1 and 5, there is depicted therein a preferred embodiment of a blade cover assembly, depicted by the reference number 10. The assembly 10 is intended for surgical use with a speculum or speculum blade 12 of the type including blade handles 60a and 60b a lower blade 16 and an upper blade 14 with opposing concavo-convex blade surfaces 18a, 18b having medial edges 62a and 62b, front end 64 and rear end 66. The blades 16 and 14 can be separated or opened to provide a channel therebetween for viewing of or surgery upon the patient. The blade cover assembly 10 hereof generally comprises:

(a) a blade cover 20 the blade cover 20 having a flexible elastic hollow sleeve-like body 22 with opposing side edges 24a, 24b a closed end 26 and an outwardly open flared end 28 adapted to be placed in covering protective relation over a speculum blade 14, 16. The body 22 is preferably formed of a polymeric resin or plastic material which is capable of undergoing a temporary memory shift when fully opened to temporarily remain fully open, thereby facilitating insertion of a speculum blade 14, 16 into the blade cover 20. The body 22, has a relaxed state. When in the relaxed state, it has a dimensionally stable concavo-convex shape with an upper convex surface 30 and a lower concave surface 32 closely resembling but slightly larger than a speculum blade 14, 16. Thus, when the cover 20 is slipped in covering relation over and in contact with the respective speculum blade 14, 16 the cover 20 is substantially unstressed and retains its concavo-convex shape intimately matching, surrounding, and closely conforming to substantially the entire length and sides of the blade surfaces 14, 16 without extensive voids therebetween. This maximizes the magnitude of the viewing channel for purposes of enhanced surgical visibility.

(b) The assembly also includes tube mount 40 disposed on the lower concave surface 32 of the blade cover 20 medial the side edges 24a, 24b, the closed end 26 and the open end 28. The tube mount 40 has a cavity 42 formed therethrough with two open ends 42a and 42b. A smoke tube 50, is insertably disposed within the cavity 42 of the tube mount 40.

The described speculum 12 is an instrument well known in the surgical art and is commonly made from stainless steel. Plastic has also been known to be used to make speculums 10. In use, the speculum 12 is manipulated to close the blades 14, 16 prior to insertion into the patient. After the insertion, the speculum 12 is manipulated to expand the blades 14, 16 until an acceptable viewing and surgical channel is available.

Before insertion of the speculum 12 into the patient, the blade cover assembly 10 is installed onto the speculum 12, the blade cover assembly 10, including the blade cover 20, the tube mount 40 and the smoke tube 50.

The speculum 12 can be used with one blade cover assembly 10 being on one blade 14 or 16 of the speculum 12 and another blade cover, such as that discussed in the aforesaid patents being fitted to the second blade 14 or 16 of the speculum 12.

Also, the speculum 12 can be used with a blade cover assembly 10 fitted on each blade 14, 16 of the speculum 12 if needed.

The blade cover 20 has a flexible sleeve-like body 22 formed by molding a single piece of polymeric plastic or resin material. The molded cover 20 has a closed end 26, side edges 24a, 24b, and an open end 28. The open end 28 of the cover 20 flares outwardly and has an opening 28a formed therein for inserting a speculum blade 14 or 16 thereinto.

The tube mount 40 is disposed on the concave wall or surface 32 of the blade cover 20. The tube mount 40 is the support for a smoke tube 50. The tube mount 40 is preferably located medial the side edges 24a, 24b and medial the closed end 26 and the open end 28. The tube mount 40 has a cylindrically shaped cavity 42 formed therethrough which receives the smoke tube 50.

The smoke tube 50 is removably inserted into the cavity 42 and through the tube mount 40 until the smoke tube 50 extends beyond each end of the tube mount 40. The exterior surface 52 of the smoke tube 50 is of sufficient diameter to prohibit casual movement of the tube 50 within the cavity 42, but still permits manual longitudinal adjustment of the smoke tube 50.

The smoke tube 50 is attachable at one end to a vacuum pump (not shown) which draws smoke from the surgical area and remains open at the other end. The smoke is the result of the surgery being performed upon tissue by surgical lasers, electrical surgical devices, heated surgical devices or the like. The vacuum pump draws the smoke from the area through the smoke tube 50.

The smoke tube 50 is a cylindrical member and has a first end 54, a second end 56 and the exterior surface or wall 52. The tube 50 also has a bore 58 formed therethrough for passage of smoke. The tube is inserted into the cavity of the tube mount until one end 54 of the tube is at the desired position to permit evacuation of smoke. The vacuum pump is attachable to the second end 56 of the tube 50 with the one end 54, accessing the area of surgery. The vacuum pump draws smoke through the tube from end 54 and through end 56.

In the preferred embodiment the smoke tube 50 is removably disposed with the blade cover 20. Because the smoke tube 50 is manually adjustable, it may be removed from the blade cover 20 while the speculum 12 is still in use.

After the surgical procedure is completed, the blade cover or covers 20 are removed from the speculum 12 blades 14, 16 and disposed of. Because the blade cover 20 was the object in contact with the patient, the cover 20 received most of the contamination—not the speculum 12. Thusly, the amount of sterilization required for the speculum 12 is substantially reduced.

In use a physician places a blade cover 20 with a tube mount 40 onto the upper blade 14 of the speculum 12. A second blade cover with or without a blade mount 40 is placed on the lower blade 16 of the speculum 12. The smoke tube 50 is inserted into and through the tube mount until one end 54 of the tube 50 extends beyond the tube mount 40 the distance desired by the physician. The speculum 12 and covers 20 are then inserted into the patient. After the insertion, the blades 14, 16 are adjusted until a sufficient viewing and surgical channel 5 is formed.

The physician attaches the other end 56 of the smoke tube 50 to the vacuum pump to draw off any smoke created by the surgical procedure. After surgery, the smoke tube 50 may be removed manually to provide greater access to the channel for examination. When the entire procedure is finished, the blade covers are removed from the speculum 12 and disposed of. The speculum 12 is then sterilized for future use.

A second embodiment of the blade cover assembly, as shown in FIGS. 2 and 4 includes a blade cover 100 with a tube mount 120 for a smoke tube 50. The blade cover 100 of this embodiment has a sleeve-like body 102 similar to the first embodiment. The body 102 has side edges 104a, 104b, a closed end 106, an open end 108, an upper convex surface 110 and a lower concave surface 112.

A tube mount 120 is disposed on the concave surface 112, medial the side edges 104a, 104b, the closed end 104 and open end 108. The tube mount 120 includes a first flexible side 122a and a second flexible side 122b with a cylindrical notch 124 formed therebetween for seating the smoke tube 150.

The smoke tube 50 is fitted into the notch 124 of the tube mount 120. The flexible sides 122a, 122b urge against the outside diameter surface 52 of the smoke tube 50 to hold the tube 50 in position. The smoke tube 50 can be manually adjusted while in the 10 notch 124, but the flexible sides 122a, 122b apply sufficient pressure to the tube 50 to prevent casual movement. This embodiment of the blade cover assembly is used similar to the preferred embodiment.

A third embodiment, as depicted in FIGS. 3 and 6, of the blade cover assembly 200 includes a flexible elastic hollow sleeve body 202 having side edges 204a, 204b a closed end 206, an open end 208, an upper convex surface 210, and a lower convex surface 212. The flexible sleeve body 202 is similar to the other embodiments.

Attached to the concave surface 212 of the blade cover assembly 200 is a cylindrical hollow smoke tube 220. The smoke tube 220 is integrally formed with the sleeve 202 as a one-piece formed unit. The smoke tube 220 has a cylindrical bore 222 formed therethrough to permit the smoke caused by the surgical process to be evacuated from one open end 254 through to the rear open end 256. End 256 is connectable to a vacuum pump via other tubing.

There has been described an improved speculum blade cover for use with surgical procedures. While there has been described particular embodiments of the invention, it will be apparent to those skilled in the art that variations may be made thereto without departing from the spirit of the invention and the scope of the appended claims.

Having thus described the invention, what is claimed is:

1. A removable blade cover system to be used with a speculum of the type including a lower blade and an upper blade, each blade having a concave blade surface and convex blade surface, said concave blade surfaces being in opposing relationship facing each other that can be separated or opened to provide a concave walled viewing channel therebetween for visual examination and treatment of a patient, the blade cover system characterized by:
    a blade cover having opposite site edges and a flexible one-piece integrally formed elastic hollow sleeve with an open end and an opposite closed end constructed to be placed in covering protective relation over a speculum blade with a concave exterior surface and convex exterior surface closely conforming to substantially the entire length and sides of the respective blade surfaces;
    a smoke tube disposed along the concave exterior surface of the blade cover with one end exposed to an exterior of said blade cover to retrieve smoke from about said blade cover and another opposite end operably connectable to a vacuum pump; and
    said smoke tube being integrally formed with and unitary with the concave surface of the blade cover and formed from the same material as the blade cover.

2. A removable blade cover system to be used with a speculum of the type including a lower blade and an upper blade, each blade having a concave blade surface and convex blade surface, said concave blade surfaces being in opposing relationship facing each other that can be separated or opened to provide a concave walled viewing channel therebetween for visual examination and treatment of a patient, the blade cover system characterized by:
    a blade cover having opposite site edges and a flexible one-piece integrally formed elastic hollow sleeve with an open end and an opposite closed end constructed to be placed in covering protective relation over a speculum blade with a concave exterior surface and convex exterior surface closely conforming to substantially the entire length and sides of the respective blade surfaces;
    a smoke tube disposed along the concave exterior surface of the blade cover with one end exposed to an exterior of said blade cover to retrieve smoke from about said blade cover and another opposite end operably connectable to a vacuum pump; and
    a tube mount being disposed on and integrally formed simultaneously with the concave surface of the blade cover, the tube mount extending from said concave exterior surface and having a cavity formed therethrough; and
    said smoke tube being insertably and removably disposed within the cavity of the tube mount.

3. A removable blade cover as defined in claim 2 further characterized by:
    said tube mount being elongated in shape with at least one wall defining an elongated substantially cylindrical cavity passing therethrough;
    said cavity having one end being sized to receive a tube therethrough with the at least one wall of the tube mount frictionally engaging said tube in a normally fixed position against unwanted accidental motion.

4. A removable blade cover as defined in claim 2 further characterized by:
    said smoke tube being a flexible elastic hollow tube.

5. A removable elastomeric speculum blade cover for removable placement over a blade of a speculum, said blade cover characterized by:
    a one piece integrally formed sleeve with an open end and an opposite closed end and with a concave exterior surface;

a smoke tube disposed along the concave exterior surface, said tube having opposite ends exposed to ambient exterior about said sleeve, one of said ends being operably connectable to a vacuum pump; and
said smoke tube being integrally formed with and unitary with the concave surface of the blade cover and formed from the same material as the blade cover.

6. A removable blade cover as defined in claim 5 further characterized by:
    said smoke tube being a flexible elastic hollow tube.

* * * * *